United States Patent
Kuboi

(10) Patent No.: US 10,436,578 B2
(45) Date of Patent: Oct. 8, 2019

(54) ENDOSCOPE APPARATUS

(71) Applicant: OLYMPUS CORPORATION, Tokyo (JP)

(72) Inventor: Toru Kuboi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 299 days.

(21) Appl. No.: 15/212,650

(22) Filed: Jul. 18, 2016

(65) Prior Publication Data

US 2016/0327781 A1 Nov. 10, 2016

Related U.S. Application Data

(63) Continuation of application No. PCT/JP2015/050936, filed on Jan. 15, 2015.

(30) Foreign Application Priority Data

Jan. 21, 2014 (JP) ................. 2014-008867

(51) Int. Cl.
*G01B 11/24* (2006.01)
*A61B 1/005* (2006.01)
(Continued)

(52) U.S. Cl.
CPC ............ *G01B 11/24* (2013.01); *A61B 1/0055* (2013.01); *G02B 6/00* (2013.01); *G02B 23/2476* (2013.01);
(Continued)

(58) Field of Classification Search
CPC ....... G01B 11/24; A61B 1/0057; A61B 1/065; A61B 2034/2061
(Continued)

(56) References Cited

U.S. PATENT DOCUMENTS

| 5,633,494 A | 5/1997 | Danisch |
| 6,563,107 B2* | 5/2003 | Danisch ................. G01B 11/18 250/227.14 |

(Continued)

FOREIGN PATENT DOCUMENTS

| JP | H05-228099 A | 9/1993 |
| JP | 2007-044402 A | 2/2007 |

(Continued)

OTHER PUBLICATIONS

International Search Report dated Apr. 7, 2015 issued in PCT/JP2015/050936.

(Continued)

*Primary Examiner* — Aaron B Fairchild
(74) *Attorney, Agent, or Firm* — Scully, Scott, Murphy & Presser, P.C.

(57) ABSTRACT

An endoscope apparatus includes an endoscope including a flexible insertion tube and a curved-shape detection sensor. The curved-shape detection sensor includes an optical fiber for propagating detection light and a sensing part provided in at least a part of the optical fiber. The curved-shape detection sensor detects a curved shape of the insertion tube based on a change of characteristics of the detection light after passing the sensing part made in accordance with a change in a curved shape of the optical fiber when the optical fiber is curved. The optical fiber is arranged on a curve axis of the insertion tube defined when the insertion tube is curved in a predetermined curve direction, or in a proximity region of the curve axis.

11 Claims, 10 Drawing Sheets

(51) Int. Cl.
*G02B 23/24* (2006.01)
*G02B 23/26* (2006.01)
*G02B 6/00* (2006.01)
*A61B 1/00* (2006.01)
*A61B 1/07* (2006.01)
*A61B 34/20* (2016.01)

(52) U.S. Cl.
CPC ............ *G02B 23/26* (2013.01); *A61B 1/0057* (2013.01); *A61B 1/00071* (2013.01); *A61B 1/07* (2013.01); *A61B 2034/2061* (2016.02); *G02B 23/2469* (2013.01)

(58) Field of Classification Search
USPC .......................................................... 600/146
See application file for complete search history.

(56) References Cited

U.S. PATENT DOCUMENTS

2009/0324161 A1 12/2009 Prisco
2011/0090486 A1 4/2011 Udd
2011/0224689 A1 9/2011 Larkin et al.
2014/0346331 A1 11/2014 Fujita

FOREIGN PATENT DOCUMENTS

| JP | 2011-245180 A | 12/2011 |
| JP | 2013-250209 A | 12/2013 |
| WO | 2013-118553 A1 | 8/2013 |

OTHER PUBLICATIONS

Chinese Office Action dated Jun. 28, 2017 in Chinese Patent Application No. 201580005257.9.
English translation of the International Preliminary Report on Patentability together with the Written Opinion dated Aug. 4, 2016 received in related International Application No. PCT/JP2015/050936.
Japanese Office Action dated Sep. 12, 2017 in Japanese Patent Application No. 2014-008867.
Extended Supplementary European Search Report dated Oct. 20, 2017 in European Patent Application No. 15 74 0236.3.

* cited by examiner

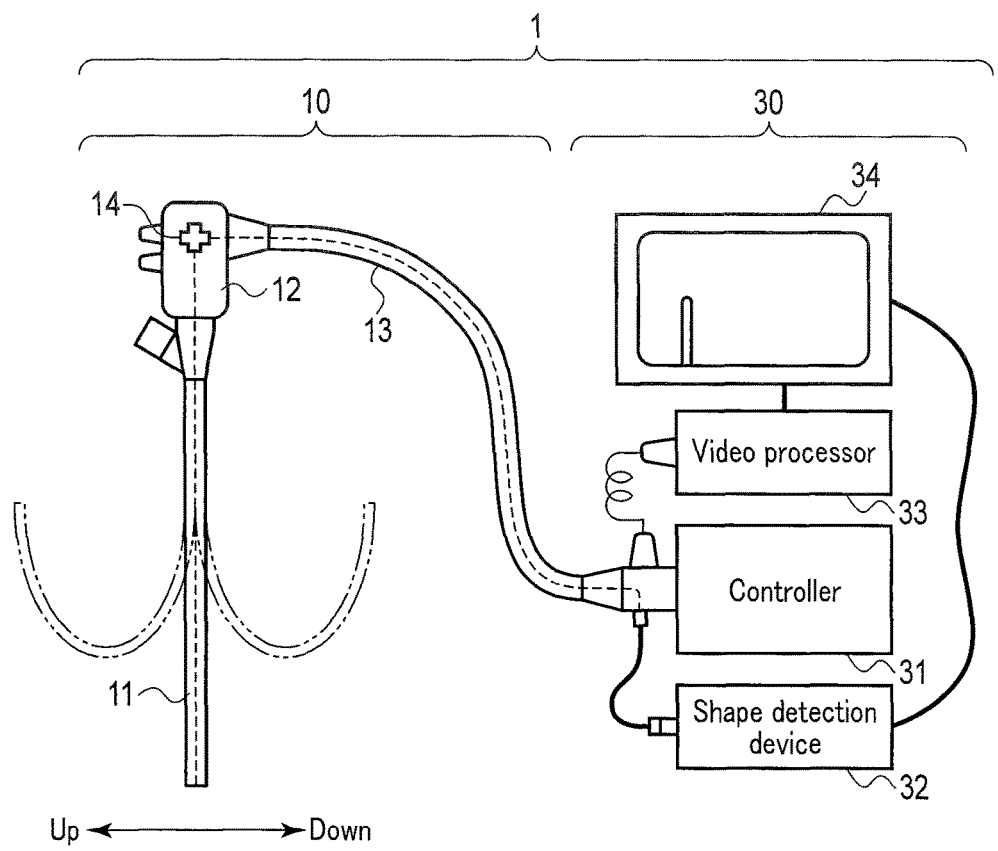
F I G. 3

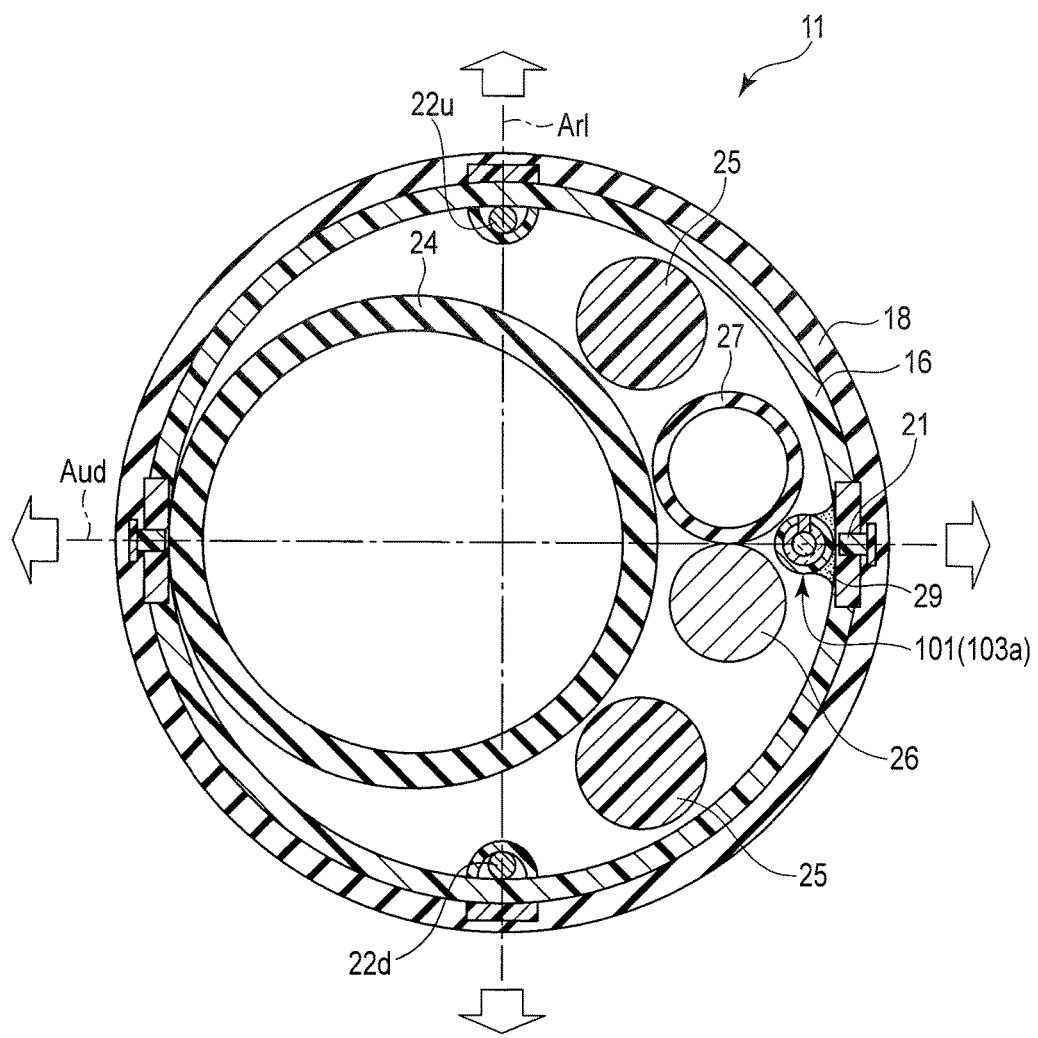
F I G. 10

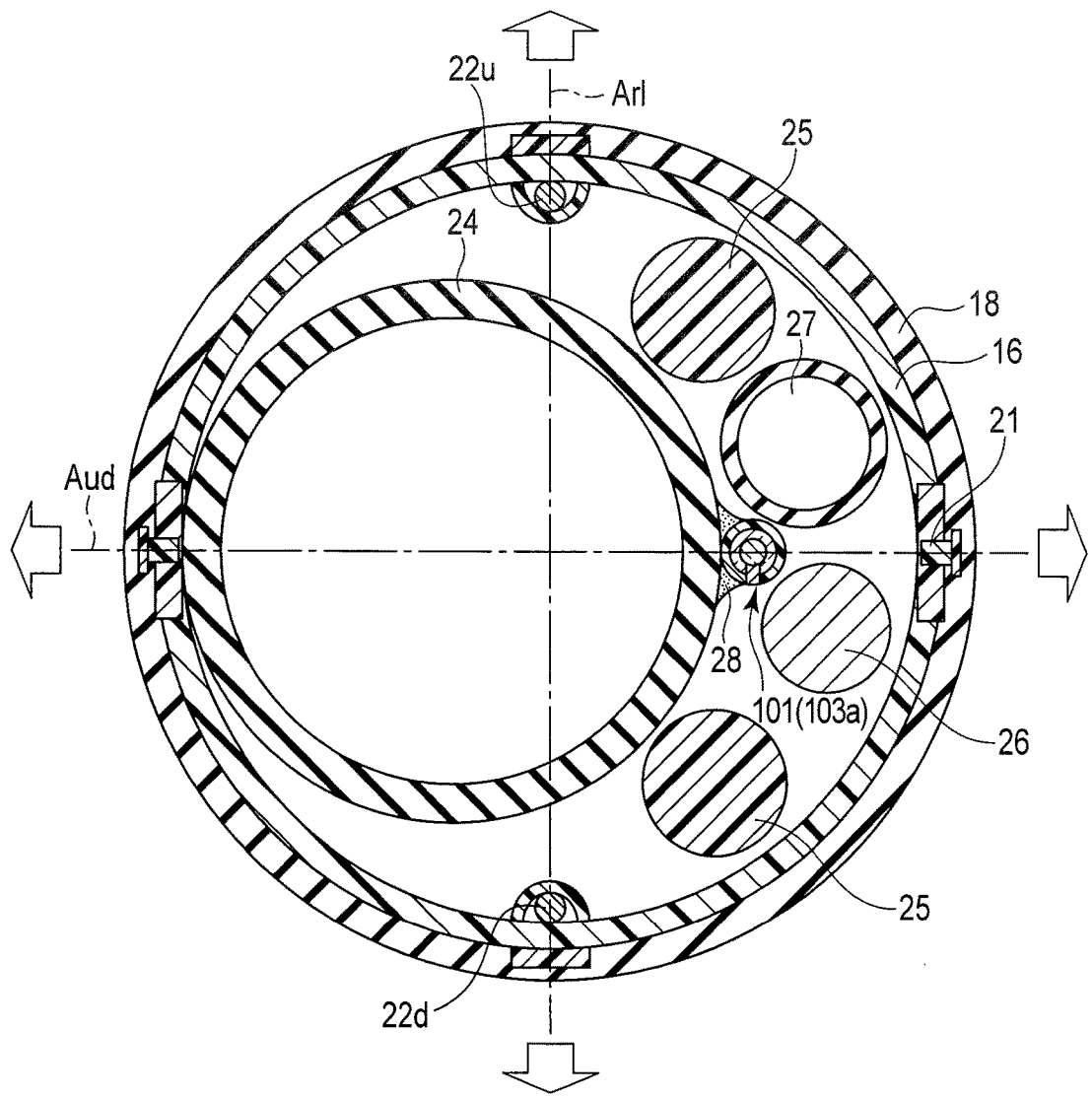
F I G. 11

ENDOSCOPE APPARATUS

CROSS-REFERENCE TO RELATED APPLICATIONS

This application is a Continuation application of PCT Application No. PCT/JP2015/050936, filed Jan. 15, 2015 and based upon and claiming the benefit of priority from prior the Japanese Patent Application No. 2014-008867, filed Jan. 21, 2014, the entire contents of all of which are incorporated herein by references.

BACKGROUND OF THE INVENTION

1. Field of the Invention

The present invention relates to an endoscope apparatus comprising a curved-shape detection sensor that detects a curved shape of a distal insertion tube of an endoscope.

2. Description of the Related Art

An endoscope comprising an elongated distal insertion tube to be inserted in an insertion target, the distal insertion tube being provided with a curved-shape detection sensor to detect a curved shape (a curved angle and a curved direction) of the distal insertion tube has been known. Such a curved-shape detection sensor is provided with a sensing part for detecting a curved shape. The curved-shape detection sensor detects the amount of change of detection light at the sensing part by a light detector, thereby detecting the curved shape of the distal insertion tube.

For example, Jpn. Pat. Appln. KOKAI Publication No. 2007-44402 discloses an endoscope apparatus comprising a light guide, curvature detection fibers, a filter, and a light receiving element. In the endoscope apparatus, a plurality of curvature detection fibers are arranged on the outer peripheral surface of a light guide in an insertion tube of an endoscope. The light guide and the curvature detection fibers extend along the insertion tube to the distal end. The filter covers an output end of the light guide and an input end of each curvature detecting fiber. A sensing part is provided in each curvature detection fiber in a predetermined position and a predetermined orientation.

In the endoscope apparatus, light output from a light source to the input end of the light guide is guided from the output end of the light guide through the filter to the input end of each curvature detection fiber. Part of the light input from the input end is lost when passing the sensing part. The endoscope apparatus detects a curved shape of the insertion tube in the sensing part based on the amount of light received at the light receiving element from the output end of each curvature detection fiber. The light guide also plays a role of transmitting illumination light to an illumination optical system at the distal end of the insertion tube.

BRIEF SUMMARY OF THE INVENTION

One embodiment of the present invention is an endoscope apparatus comprising an endoscope including a flexible insertion tube and a curved-shape detection sensor including an optical fiber for propagating detection light and a sensing part provided in at least a part of the optical fiber, the curved-shape detection sensor configured to detect a curved shape of the insertion tube based on a change of characteristics of the detection light after passing the sensing part made in accordance with a change in a curved shape of the optical fiber when the optical fiber is curved, wherein the optical fiber is arranged on a curve axis of the insertion tube defined when the insertion tube is curved in a predetermined curve direction, or in a proximity region thereof.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 shows an overall configuration of an endoscope apparatus including an endoscope equipped with the curved-shape detection sensor.

FIG. 10 is a radial cross-sectional view of the distal insertion tube of the endoscope apparatus in the second embodiment.

FIG. 11 is a radial cross-sectional view of the distal insertion tube of the endoscope apparatus in a variant of the second embodiment.

DETAILED DESCRIPTION OF THE INVENTION

First Embodiment (Curve Shape Detection Sensor)

The configuration and operation of the curved-shape detection sensor (hereinafter merely referred to as "sensor") 101 will be described.

Figure 1:
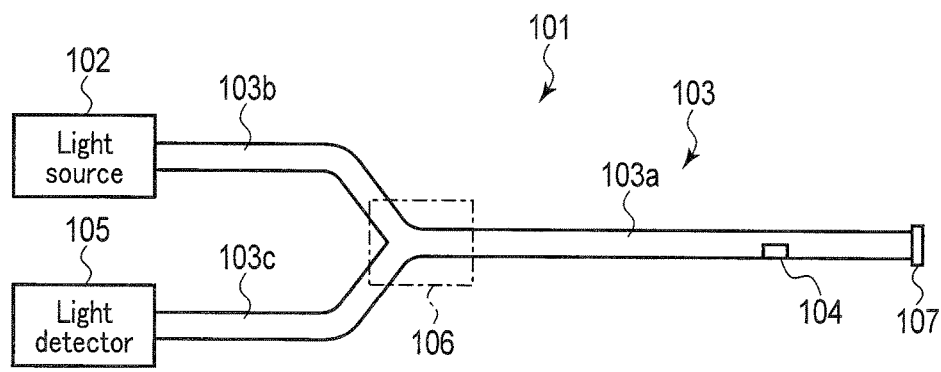
FIG. 1 is a schematic diagram illustrating principles of a curved-shape detection sensor.

FIG. 1 is a schematic diagram illustrating principles of the sensor 101. The sensor 101 includes a light source 102, an optical fiber 103, and a light detector 105. The optical fiber 103 is connected to the light source 102 and the light detector 105. The light source 102 is, for example, an LED light source or a laser light source, and outputs detection light having desired wavelength characteristics. The optical fiber 103 propagates the detection light output from the light source 102. The light detector 105 detects the detection light guided through the optical fiber 103.

The optical fiber 103 includes a detection light optical fiber 103a, a light-supplying optical fiber 103b, and a light-receiving optical fiber 103c, which are three branches branching from a coupler (optical coupler) 106. Namely, the optical fiber 103 is formed by connecting two light guiding path members, i.e., light-supplying optical fibers 103b and the light-receiving fiber 103c, to one light guiding path member, i.e., the detection light optical fiber 103a. The proximal end of the light-supplying optical fiber 103b is connected to the light source 102. A reflector 107 for reflecting propagated light is provided at the distal end of the detection light optical fiber 103a. The reflector 107 is, for example, a mirror. The proximal end of the light-receiving optical fiber 103c is connected to the light detector 105.

The light-supplying optical fiber 103b propagates light output from the light source 102, and guides it to the coupler 106. The coupler 106 guides large part of light input from the light-supplying optical fiber 103b to the detection light optical fiber 103a, and guides at least part of the light reflected by the reflector 107 to the light-receiving optical fiber 103c. The light from the light-receiving optical fiber 103c is received by the light detector 105. The light detector 105 photoelectrically converts the received detection light, and outputs an electrical signal representing an amount of the detection light.

Figure 2:
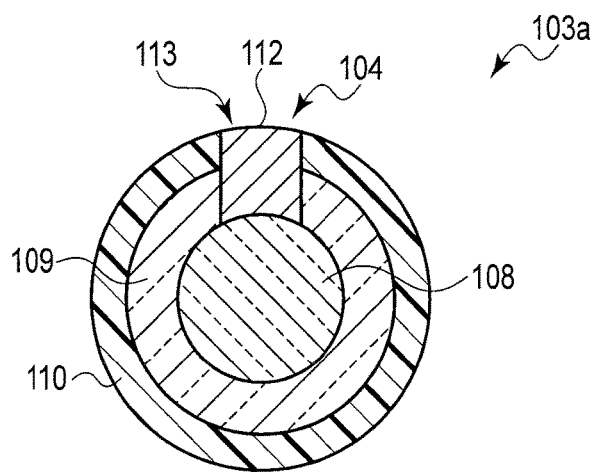
FIG. 2 is a radial cross-sectional view of a detection light optical fiber.

FIG. 2 is a radial cross-sectional view of the detection light optical fiber 103a. The detection light optical fiber 103a includes a core 108, a cladding 109 that covers the outer peripheral surface of the core 108, and a coating 110 that covers the outer peripheral surface of the cladding 109. The detection light optical fiber 103a includes at least one sensing part 104 (three sensing parts 104a-104c in the first embodiment; see FIGS. 6 and 7). The sensing part 104 is provided in only a part of the outer periphery of the optical fiber, and changes the characteristics of the detection light that passes through the sensing part 104 in accordance with a change of the curved shape of the detection light optical fiber 103a.

The sensing part 104 includes a light opening 112 formed by removing a part of each of the cladding 109 and the coating 110 to expose the core 108, and an optical characteristic conversion member 113 formed in the light opening 112. The light opening 112 does not necessarily expose the core 108 as long as it allows light that passes through the detection light optical fiber 103a to reach the light opening 112. The optical characteristic conversion member 113 converts the characteristics of the light guided through the detection light optical fiber 103a, and is, for example, a guided light loss member (light absorber) or a wavelength conversion member (phosphor). In the following description, let us assume that the optical characteristic conversion member is a guided light loss member.

In the sensor 101, the light supplied from the light source 102 is guided through the detection light optical fiber 103a as described above. When the light enters the optical characteristic conversion member 113 of the sensing part 104, part of the light is absorbed by the optical characteristic conversion member 113, which causes loss of guided light. The amount of this loss of guided light varies in accordance with the amount of curve of the light-receiving optical fiber 103c.

For example, even when the detection light optical fiber 103a is straight, a certain amount of light is lost in the optical characteristic conversion member 113 in accordance with the width of the light opening 112. Let us assume that the amount of lost light in the straight state is a reference amount. When the optical characteristic conversion member 113 is provided on the outer peripheral surface (outside), the amount of lost guided light is larger than the reference amount of lost guided light. When the optical characteristic conversion member 113 is provided on the inner peripheral surface (inside) in a state where the detection light optical fiber 103a is curved, the amount of lost guided light is smaller than the reference amount of lost guided light.

The change in the amount of lost guided light is reflected in the amount of detection light received by the light detector 105, i.e., the output signal of the light detector 105. Accordingly, the curved shape in the position of the sensing part 104 of the sensor 101, i.e., the position where the optical characteristic conversion member 113 is provided, can be obtained based on the output signal of the light detector 105. The detection light optical fiber 103a of the sensor 101 is integrally attached to a long flexible curved target to be measured, which is the distal insertion tube of the endoscope in the present embodiment, along the target. The sensor 101 is attached to a proper position of the distal insertion tube by aligning a desired detection position of the distal insertion tube with the sensing part 104 of the sensor 101. Then, the detection light optical fiber 103a is curved following the flexible movement of the distal insertion tube, and the sensor 101 detects the curved shape of the distal insertion tube as described above.

(Configuration of Endoscope Apparatus)

FIG. 3 shows an overall configuration of the endoscope apparatus 1. The endoscope apparatus 1 includes an endoscope main body (endoscope) 10 into which at least the detection light optical fiber 103a of the sensor 101 is incorporated and an apparatus main body 30. The apparatus main body 30 includes a controller 31, a shape detection device 32, a video processor 33, and a monitor 34. The controller 31 controls given functions of the endoscope main body 10, the shape detection device 32, and the video processor 33 as well as those of peripheral devices connected thereto. Although the sensor 101 is not shown in FIG. 3, the endoscope apparatus 1 includes the structures of the sensor 101 shown in FIG. 1.

The endoscope main body 10 includes the flexible distal insertion tube 11 to be inserted in an insertion target, an operation unit main body 12 coupled to the proximal side of the distal insertion tube 11, and a code section 13 extending from the operation unit main body 12. The endoscope main body 10 is detachably connected to the apparatus main body 30 via the code section 13, and communicates with the apparatus main body 30. The operation unit main body 12 includes an operation dial 14 that inputs an operation for curving the distal insertion tube 11 in at least two specific directions (such as upward and downward) with a desired curvature. The code section 13 contains, for example, member A 25 and member B 26 to be described later. The endoscope apparatus 1 includes the sensor 101, and the detection light optical fiber 103a of the sensor 101 is arranged in the distal insertion tube 11 of the endoscope main body 10. As described above, when the detection light optical fiber 103a is curved, the sensor 101 detects the curved shape of the distal insertion tube 11 based on the change of the characteristics of the detected light that has passed through the sensing part 104, which is made in accordance with the change in its curved shape.

The shape detection device 32 is connected to the light detector 105 of the sensor 101, and calculates the curved shape of the distal insertion tube 11 based on the output signal from the light detector 105. The calculated curved shape is transmitted from the shape detection device 32 to the monitor 34 and is displayed on the monitor 34.

The video processor 33 processes an electrical signal from an image pickup element (not shown) at the distal end of the endoscope, and sends the processed electrical signal to the monitor 34, and an image of the inside of the insertion target is displayed on the monitor 34.

Figure 4:
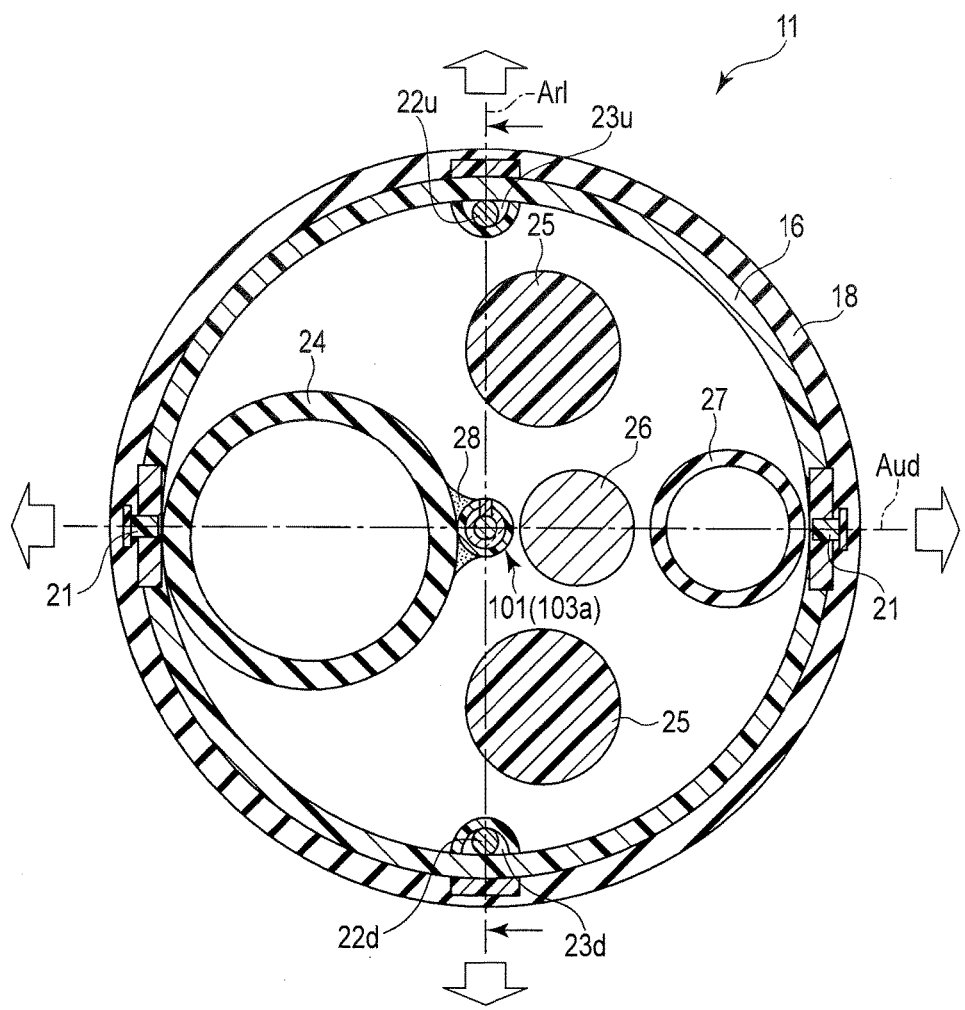
FIG. 4 is a radial cross-sectional view of a distal insertion tube of the endoscope apparatus in the first embodiment.
Figure 5:
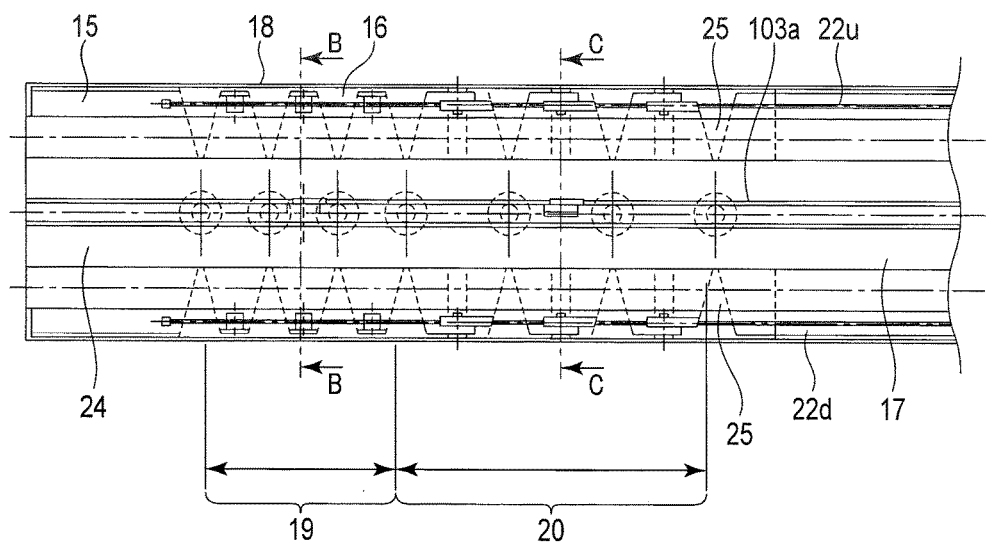
FIG. 5 is an axial cross-sectional view of the distal insertion tube of the endoscope apparatus in the first embodiment.

FIGS. 4 and 5 are radial and longitudinal cross-sectional views of the distal insertion tube 11 in the first embodiment, respectively. The distal insertion tube 11 is an elongated cylindrical member on the endoscope main body distal side. As shown in FIG. 5, the distal insertion tube 11 includes a distal member 15, a plurality of curve tube 16, and a corrugated tube 17. The plurality of curve tubes 16 are coupled in series with the distal member 15 provided on the distal side, and the corrugated tube 17, which is curved in any direction, is coupled to the proximal side of the curve tubes 16. The outer peripheral surface of each of the curve tubes 16 and the corrugated tube 17 is covered with flexible coating 18.

As shown in FIG. 5, the curve tubes 16 are divided into an operation curve portion 19 on the distal side, which curves only in two directions, upward and downward (UP/DOWN; hereinafter referred to as "UD"), and a free curve portion 20 on the proximal side, which curves in four directions, upward, downward, rightward and leftward (RIGHT/LEFT: hereinafter referred to as "RL") (in any direction of 360 degrees by combination). Namely, the curve tubes 16 at the operation curve portion 19 curve in the UD direction relative to the UD curve axis $A_{ud}$ (see FIG. 4), and the curve tubes 16 at the free curve portion 20 curve in the UD direction relative to the UD curve axis $A_{ud}$ and in the RL direction relative to the RL curve axis $A_{rl}$ orthogonal to the UD curve axis $A_{ud}$ (also see FIG. 4).

In the range of the operation curve portion 19, as shown in FIG. 4, the curve tubes 16 are coupled to each other by rivets 21 on the UD curve axis $A_{ud}$ so as to turn around the UD curve axis $A_{ud}$. In the range of the free curve portion 20, the curve tubes 16 are coupled to rotate around the RL curve axis $A_{rl}$, which is arranged to deviate by 90 degrees with respect to the axial center, in addition to the UD curve axis $A_{ud}$.

Distal ends of an operation wire 22*u* for curving upward and an operation wire 22*d* for curving downward are fixed to the distal member 15 of the distal insertion tube 11. The operation wires 22*u* and 22*d* are inserted respectively in concave portions 23*u* and 23*d* of the curve tubes 16 in the range of the operation curve portion 19, and their proximal ends are coupled to the operation dial 14 of the operation unit main body 12. Accordingly, the distal insertion tube 11 is curved upward when operation wire 22*u* is pulled, and is curved downward when operation wire 22*d* is pulled in accordance with rotation of the operation dial 14 by the operator.

The UD curve axis $A_{ud}$ and the RL curve axis $A_{rl}$ are rotational axes defined by the rivets 21, and exist for each set of rivets 21 coupling the curve tubes 16. Each set of the rivets 21 are parallel to each other, and are parallel to a virtual curve center axis of the case where the distal insertion tube 11 is viewed as a whole. Instead of the rivets 21 defining the curve direction, the curve tubes 16 may have a groove formed in, for example, a pipe member to define the curve direction, which also provides a virtual curve center axis. Such a virtual curve center axis is set in a direction approximately orthogonal to the operation wires 22*u* and 22*d* in any configuration.

Inside the distal insertion tube 11, a channel tube 24, a member A 25, a member B 26 and a member C 27 extend in the longitudinal direction. The members A-C are those selected from a curve tube, a light guide, an image guide, an electrical signal wire, a power-supplying wire, an air pipe, a water pipe, and an operation wire etc. The channel tube 24 is a cylindrical tube in which a treatment tool, such as an ultrasonic probe or a forceps, can be inserted. For example, the distal end of the light guide is connected to an illumination optical system (not shown) at the endoscope main body distal end, and the proximal end thereof is connected to the light source (not shown) via the code section 13. For example, the distal end of the electrical signal wire is connected to an image pickup device (not shown) at the endoscope main body distal end, and the proximal end thereof is connected to the controller 31 (not shown) via the code section 13.

Inside the distal insertion tube 11, the light detection optical fiber 103*a* of the sensor 101 is arranged on the UD curve axis $A_{ud}$ or the RL curve axis $A_{rl}$, or in the proximity region thereof, such as in the proximity to the intersection between the UD curve axis $A_{ud}$ and the RL curve axis $A_{rl}$ in FIG. 4. The details of the "proximity region" are described later. For example, if the light detection optical fiber 103*a* is arranged in proximity to the intersection between the UD curve axis $A_{ud}$ and the RL curve axis $A_{rl}$, the outer diameter of the channel tube 24 is less than half the inner diameter of the curve tube 16.

The light detection optical fiber 103*a* is bonded to the outer peripheral surface of the channel tube 24 by an adhesive 28 in such a manner that the light detection optical fiber 103*a* can be curved together with the channel tube 24. Accordingly, the channel tube 24 serves as a sensor holding member. The bonding is not limited to adhesion, and may be fusion.

The contained member in the distal insertion tube 11 that serves as the sensor holding member is not limited to the channel tube 24, and may be the operation wire 22*u* or 22*d*, channel tube 24, member B 26, or member C 27 etc., which curves within the distal insertion tube 11. However, the channel tube 24 is the largest in the cross-section area among the contained members in the distal insertion tube 11, and thus has higher torsional rigidity than the other contained members. When the contained member to which the detection light optical fiber 103*a* is attached is twisted, the position of the sensing part 104 is deviated, and the detection accuracy of the curved shape is decreased. Therefore, it is desirable that the contained member to which the detection light optical fiber 103*a* is attached has high torsional rigidity. Consequently, it is desirable that the contained member to which the detection light optical fiber 103*a* is attached has a large outer diameter. Accordingly, in the present embodiment, the channel tube 24, which has the largest outer diameter among the structural members within the distal insertion tube 11, is used as the sensor holding member.

Figure 6:
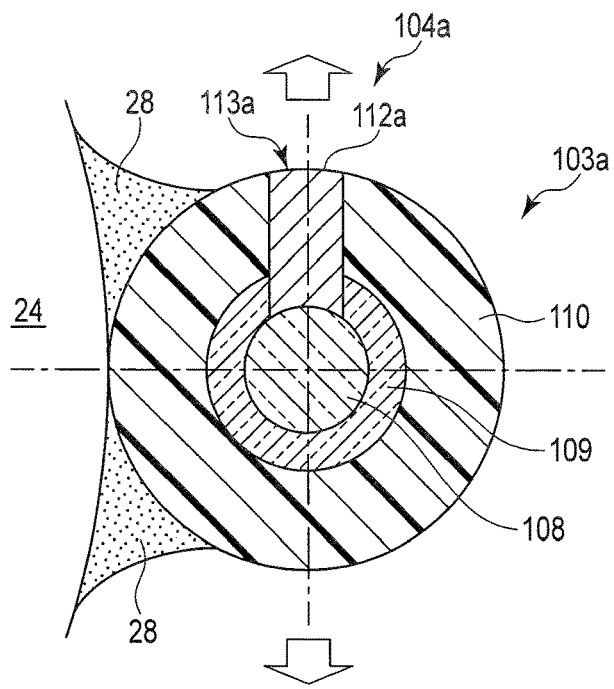
FIG. 6 is a radial cross-sectional view of a part of the distal insertion tube taken along line B-B in FIG. 5.

FIG. 6 is a cross-sectional view including the sensing part 104*a* in the operation curve portion 19 (light opening 112*a* and optical characteristic conversion member 113*a*), taken along line B-B in FIG. 5. Since the operation curve portion 19 curves only in the UD direction, the operation curve portion 19 is provided with only one sensing part 104*a* in an orientation corresponding to the UD direction, i.e., in a position orthogonal to the UD curve axis $A_{ud}$.

Figure 7:
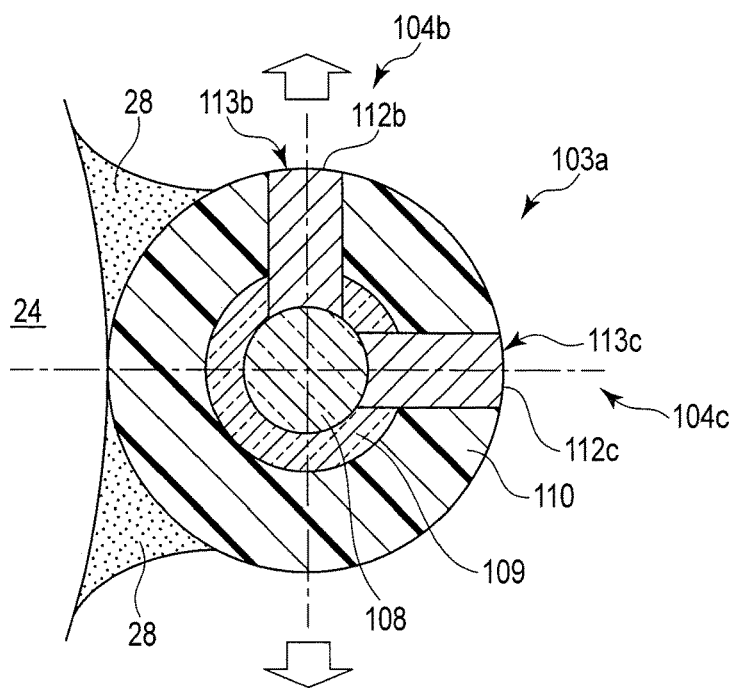
FIG. 7 is a radial cross-sectional view of a part of the distal insertion tube taken along line C-C in FIG. 5.

FIG. 7 is a cross-sectional view including the sensing part 104*b* (light opening 112*b* and optical characteristic conversion member 113*b*) and the sensing part 104*c* (light opening 112*c* and optical conversion member 113*c*) in the free curve portion 20, taken along line C-C in FIG. 5. Since the free curve portion 20 curves in the UD direction and the RL direction, the free curve portion 20 is provided with the sensing part 104$b$ in an orientation corresponding to the UD direction, i.e., in a position orthogonal to the UD curve axis $A_{ud}$, and with the sensing part 104$c$ in an orientation corresponding to the RL direction, i.e., in a position orthogonal to the RL curve axis $A_{rl}$. Accordingly, the sensing parts 104$b$ and 104$c$ are provided to be orthogonal to each other.

Regarding the sensor 101, as described above, the detection direction of the curved shape of the detection light optical fiber 103$a$ is determined based on the orientation of the sensing part 104 provided in the detection light optical fiber 103$a$. In the present embodiment, the detection direction is orthogonal to the curve axis. Namely, the sensing parts 104$a$ and 104$b$ are used for detecting the curved shape in the UD direction orthogonal to the UD curve axis $A_{ud}$ in the operation curve portion 19 and the free operation portion 20, respectively. The detection section 104$c$ is used for detecting the curved shape in the RL direction orthogonal to the RL curve axis $A_{rl}$ in the free operation portion 20. Accordingly, the detection direction of at least one sensing part of a plurality of sensing parts is orthogonal to the UD curve axis $A_{ud}$, and at least one sensing part is parallel to the UD curve axis $A_{ud}$.

The curve axis of the operation curve portion 19 operable by the operation wires 22$u$ and 22$d$, i.e., the curve axis in the direction of curve made by the operations of the operation wires 22$u$ and 22$d$, is defined as the main curve axis. In the present embodiment, the main curve axis is the UD curve axis $A_{ud}$. For example, when there are a plurality of curve axes in the operation curve portion 19, the curve axis of the larger curve angle is the main curve axis.

(Advantages)

When the distal insertion tube 11 is curved by an operation of the operation wires 22$u$ and 22$d$, or by contacting, for example, an insertion target and receiving external force, the detection light optical fiber 103$a$ of the sensor 101 is curved in accordance with the distal insertion tube 11. At this time, the bending stress caused in the sensor 101 by the curve can be reduced in the present embodiment because the detection light optical fiber 103$a$ is arranged on the UD curve axis $A_{ud}$ or the RL curve axis $A_{rl}$, or in a proximity region thereof. Accordingly, an endoscope apparatus having a reliable shape detection sensor can be provided.

Furthermore, according to the present embodiment, the detection direction of each of the light openings 112$a$-112$c$ is set in accordance with the UD curve axis $A_{ud}$ and the RL curve axis $A_{rl}$, i.e., to be orthogonal to those curve axes; therefore, the curved shape can be detected with high sensitivity.

Moreover, according to the present embodiment, because the detection light optical fiber 103$a$ of the sensor 101 is attached to the channel tube 24 which has high torsional rigidity, i.e., is thick (has a large outer diameter), the detection light optical fiber 103$a$ is less twisted. Therefore, the curved shape of the channel tube 24, i.e., the distal insertion tube 11, can be detected without a decrease of the detection accuracy due to a twist.

(Proximity Region of Curve Shape Detection Sensor)

As described above, the detection light optical fiber 103$a$ is arranged on the UD curve axis $A_{ud}$ or the RL curve axis $A_{rl}$, or in a proximity region thereof. The "proximity region" is described in detail below.

Figure 8:
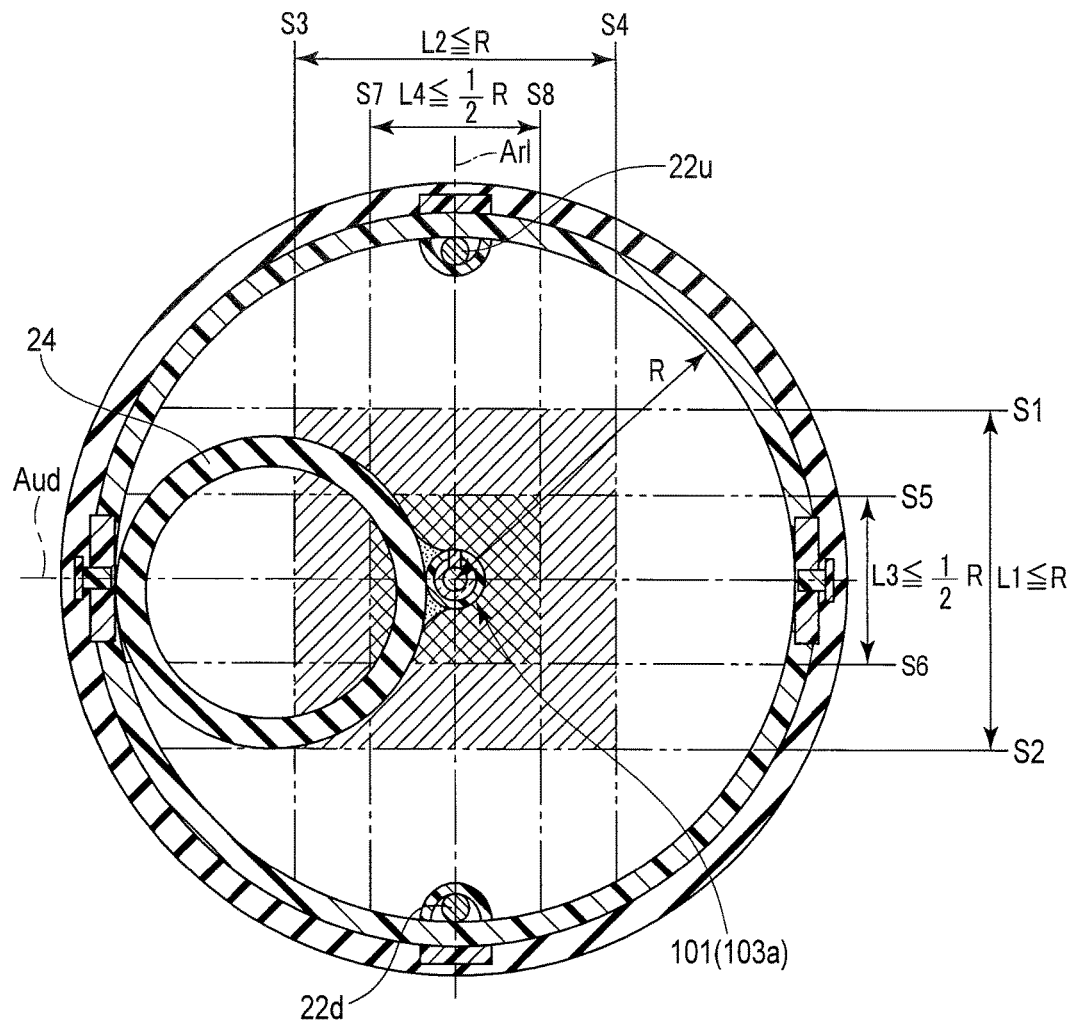
FIG. 8 is a radial cross-sectional view showing a curve axis proximity region and attachment region of the distal insertion tube in the first embodiment.

FIG. 8 is a cross-sectional view showing a proximity region to which the detection light optical fiber 103$a$ of the curved-shape detection sensor 101 is attached in the first embodiment, as well as a first attachment region and a second attachment region. The inner radius of the curve tube 16 is R. Let us assume that two straight lines S1 and S2 at a distance of R/2 from the UD curve axis $A_{ud}$ and parallel to the UD curve axis $A_{ud}$, and two straight lines S3 and S4 at a distance of R/2 from the RL curve axis $A_{rl}$ and parallel to the RL curve axis $A_{rl}$ are drawn. The region within the curve tube 16 between straight lines S1 and S2, i.e., the region defined by the width of radius R with the UD curve axis $A_{ud}$ as the center, is defined as a UD curve axis proximity region. The region within the curve tube 16 between straight lines S3 and S4, i.e., the region defined by the width of radius R with the RL curve axis $A_{rl}$ as the center, is defined as an RL curve axis proximity region. The detection light optical fiber 103$a$ of the sensor 101 is arranged on the UD curve axis $A_{ud}$ or the RL curve axis $A_{rl}$, or in a proximity region thereof, i.e., the UD curve axis proximity region or the RL curve axis proximity region.

Arranging the detection light optical fiber 103$a$ of the sensor 101 within the proximity region reduces the bending stress which may damage the optical fiber, and enables providing an endoscope apparatus having a reliable shape detection function.

The region surrounded by those straight lines S1-S4 is described as the first attachment region (indicated by hatching with falling diagonal strokes from top right to bottom left in the figure). In other words, the first attachment region is the inside of the square with the center of the curve tube 16 as the center and the sides having lengths L1 and L2 equal to R. Let us assume that two straight lines S5 and S6 at a distance of R/4 from the UD curve axis $A_{ud}$ and parallel to the UD curve axis $A_{ud}$, and two straight lines S7 and S8 at a distance of R/4 from the RL curve axis $A_{rl}$ and parallel to the RL curve axis $A_{rl}$ are drawn. The region surrounded by those four straight lines S5-S8 is defined as the second attachment region (indicated by hatching with diagonal strokes falling from top left to bottom right in the figure). In other words, the second attachment region is the inside of the square with the center of the curve tube 16 as the center and the sides having lengths L3 and L4 equal to R/2. The second attachment region is included in the first attachment region.

The detection light optical fiber 103$a$ is attached to the outer peripheral surface of the sensor holding member (channel tube 24 in FIG. 8) by adhesion or fusion preferably within the first attachment region, more preferably within the second attachment region.

It has been empirically known that providing the sensor 101 within the first attachment region can ensure the endurance required for an endoscope. In particular, providing the sensor 101 within the second attachment region can further improve the detection accuracy because the second attachment region is closer to the center of the distal insertion tube 11 than the first attachment region.

Accordingly, the present embodiment can provide an endoscope apparatus that reduces the bending stress and detects a curved shape with high accuracy by attaching the sensor 101 to a proximity region of the UD curve axis $A_{ud}$ or the RL curve axis $A_{rl}$, or the first attachment region or the second attachment region in the proximity to the intersection between the UD curve axis $A_{ud}$ and the RL curve axis $A_{rl}$.

The above-mentioned widths R/2 and R/4 are large when the distal insertion tube is thick, and small when the distal insertion tube is thin. Since an endoscope including a thick distal insertion tube does not usually curve much (the minimum bend radius is usually large), the widths may be large; however, because an endoscope including a thin distal insertion tube usually curves tightly (the minimum bend radius is usually small), the widths need to be small.

Variant of First Embodiment

Figure 9:
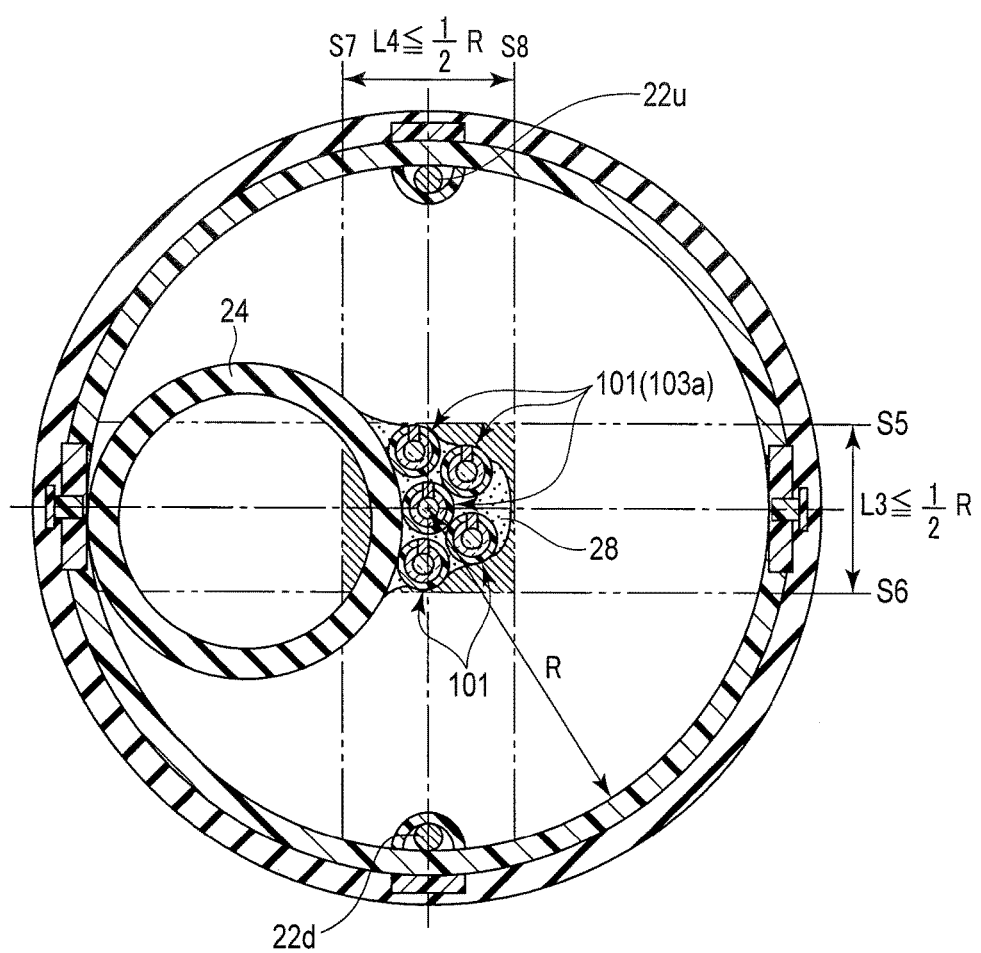
FIG. 9 is a radial cross-sectional view showing the attachment region of the distal insertion tube in a variant of the first embodiment.

FIG. 9 is a cross-sectional view showing an attachment region to which the detection light optical fiber 103a of the curved-shape detection sensor 101 is attached in a variant of the first embodiment. FIG. 9 only shows an attachment region surrounded by two straight lines S5 and S6 at a distance of R/4 from the UD curve axis $A_{ud}$ and parallel to the UD curve axis $A_{ud}$, and two straight lines S7 and S8 at a distance of R/4 from the RL curve axis $A_{rl}$ and parallel to the RL curve axis $A_{rl}$.

A plurality of detection light optical fibers 103a may be arranged as long as they are within the attachment region. For example, in the variant shown in FIG. 9, five detection light optical fibers 103a are attached to the outer peripheral surface of the channel tube 24 within the attachment region.

Even such a variant can provide an endoscope apparatus having a reliable shape detection sensor while ensuring the endurance required for an endoscope.

Second Embodiment

The second embodiment of the present invention will be described with reference to FIG. 10. Hereinafter, structural members similar to those in the first embodiment are assigned with the same reference numerals, and descriptions thereof are omitted while describing only the parts different from the first embodiment.

FIG. 10 is a radial cross-sectional view of the distal insertion tube 11 in the second embodiment. In the present embodiment, to enable insertion of a thick treatment tool in the channel tube 24, the channel tube 24 is configured to have a larger inner diameter than in the first embodiment and have an outer diameter that is half or larger than half the inner diameter of the curve tube 16.

The detection light optical fiber 103a of the sensor 101 is attached to the inner wall of the curve tube 16 by the adhesive 29 on the UD curve axis $A_{ud}$, which is the main curve axis, or in the proximity thereto, or the intersection between the UD curve axis $A_{ud}$ and the curve tube 16 in FIG. 10. The "proximity" here is the same as the UD curve axis proximity region in the first embodiment. The curve tube 16 has the largest outer diameter among the curvable members included in the distal insertion tube 11, and is made of a metal material. Namely, the curve tube 16 has the highest torsional rigidity among the members being capable of curving included in the distal insertion tube 11.

The light detection optical fiber 103a may be attached to the channel tube 24, member B 26, or C 27, as long as the contained member crosses the UD curve axis $A_{ud}$. The attachment length in the axial direction, over which the detection light optical fiber 103a is attached to the contained member, is within the range of the operation curve portion 19, the rotation of which relative to the UD curve axis $A_{ud}$ is restricted.

In the present embodiment, the curve tube 16, which is a structural member of the distal insertion tube 11, serves as the sensor holding member. Attaching the sensor 101 to the curve tube 16, which has the highest torsional rigidity among the members being capable of curving included in the distal insertion tube 11, can achieve accurate detection with few twists of the sensor 101, at least regarding detection of the curved shape in the operation curve portion 19.

The present embodiment can achieve a more accurate detection of the curved shape of the operation curve portion 19 than that of the first embodiment. In addition, the present embodiment can improve the accuracy in curved shape detection of an endoscope that allows use of a thicker treatment tool.

Variant of Second Embodiment

FIG. 11 is a radial cross-sectional view of the distal insertion tube 11 in a variant of the second embodiment. In the present variant, the detection light optical fiber 103a of the sensor 101 is bonded to the channel tube 24 by the adhesive 28 on the UD curve axis $A_{ud}$ or in a proximity region thereof. When the detection light optical fiber 103a is arranged on one of the UD curve axis $A_{ud}$ and the RL curve axis $A_{rl}$, it is desirable to arrange the detection light optical fiber 103a on the main curve axis. When the detection light optical fiber 103a is arranged on the main curve axis or in a proximity region thereof, it is desirable to arrange the detection light optical fiber 103a on a member that can be arranged as close as possible to the other curve axis.

The present variant can reduce the bending stress caused in the sensor 101 when the distal insertion tube 11 is curved more than in the second embodiment. Accordingly, an endoscope with higher reliability regarding detection accuracy can be provided.

Figure 12:
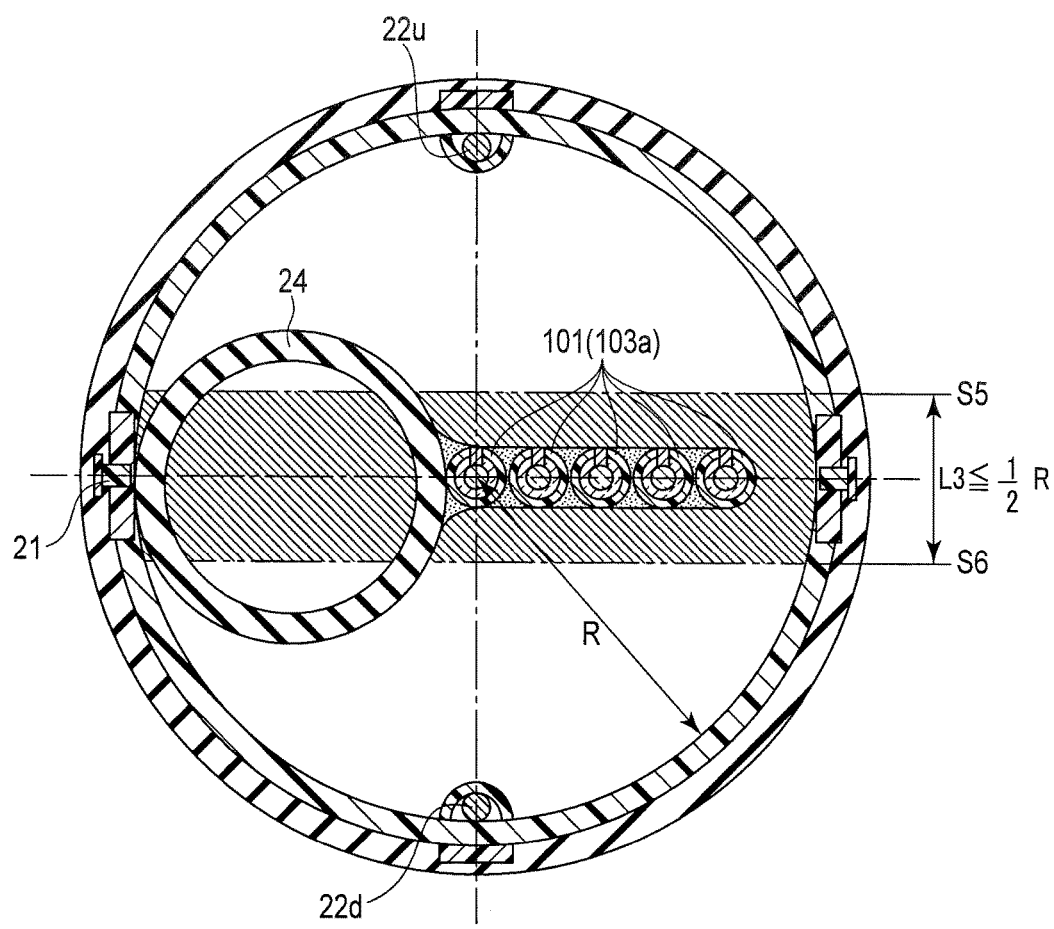
FIG. 12 is a radial cross-sectional view showing the curved axis proximity region of the distal insertion tube in the variant of the second embodiment.

FIG. 12 is a cross-sectional view showing a proximity region to which the detection light optical fiber 103a of the curved-shape detection sensor 101 is attached in the variant of the second embodiment. The proximity region is the region within the curve tube 16 between two straight lines S5 and S6 at a distance of R/4 from the UD curve axis $A_{ud}$ and parallel to the UD curve axis $A_{ud}$, i.e., the UD curve axis proximity region defined by the width of half the radius R with the UD curve axis $A_{ud}$ as the center. The detection optical fiber 103a of the sensor 101 is attached to the outer peripheral surface of the channel tube 24 by adhesion or fusion within the proximity region, for example, at an intersection between the channel tube 24 and the UD curve axis $A_{ud}$ or in the proximity thereto.

As described above, it has been empirically known that providing the sensor 101 on the curve axis or within a proximity region thereof can ensure the endurance required for an endoscope. Accordingly, the present variant can also provide an endoscope apparatus comprising a curved-shape detection sensor that accurately detects a curved shape by setting the region for attaching the sensor 101 on the UD curve axis $A_{ud}$, or in a proximity region thereof.

The number of the detection light optical fibers 103a of the sensor 101 need not be five as shown in FIG. 12, and may be any number as long as the detection light optical fibers 103a are within the attachment region and can be held on the outer peripheral surface of the channel tube 24, which serves as the sensor holding member.

The present invention is not limited to the foregoing embodiment described above, but it is evident to a person with ordinary skill in the art that various improvements and modifications can be made without departing from the subject matter of the present invention.

What is claimed is:
1. An endoscope apparatus, comprising:
an endoscope including a flexible insertion tube including a bending portion configured to bend in accordance with an instruction from an operator about one or more curve axes passing through the bending portion, the one or more curve axes being orthogonal to a longitudinal axis of the bending portion; and a curved-shape detection sensor including an optical fiber for propagating detection light and a sensing part provided in at least a part of the optical fiber, the curved-shape detection sensor configured to detect a curved shape of the insertion tube based on a change of characteristics of the detection light after passing the sensing part made in accordance with a change in a curved shape of the optical fiber when the optical fiber is curved, wherein the optical fiber is arranged on the one or more curve axes or in a proximity region of the one or more curve axes, the optical fiber being attached to and held by an outer peripheral surface of a sensor holding member in the insertion tube, the sensor holding member being a structural member arranged inside the insertion tube and having a higher torsional rigidity than at least one other structural member included within the insertion tube.

2. The endoscope apparatus according to claim 1, wherein the optical fiber is arranged in the proximity region and the proximity region is a region between two straight lines parallel to the one or more curve axes and at a distance equal to or smaller than half of a radius of the insertion tube from the one or more curve axes.

3. The endoscope apparatus according to claim 1, wherein the one or more curve axes includes a first curve axis and a second curve axis orthogonal to the first curve axis, and the optical fiber is arranged in the proximity region and the proximity region is a region surrounded by a pair of first straight lines parallel to the first curve axis and separated by a distance equal to or smaller than half a radius of the insertion tube from the first curve axis and by a pair of second straight lines parallel to the second curve axis and separated by a distance equal to or smaller than half the radius of the insertion tube from the second curve axis.

4. The endoscope apparatus according to claim 1, wherein the optical fiber is arranged at an intersection between a central axis of the sensor holding member and a curve axis of the one or more curved axes.

5. The endoscope apparatus according to claim 4, wherein the sensor holding member has an outer diameter larger than any other structural member of the insertion tube.

6. The endoscope apparatus according to claim 5, wherein the sensor holding member comprises a channel tube.

7. The endoscope apparatus according to claim 1, wherein the one or more curve axes includes a first curve axis and a second curve axis orthogonal to the first curve axis, and the optical fiber is held on a one of the first and second curve axes having a greater curve angle.

8. The endoscope apparatus according to claim 1, wherein the one or more curve axes includes a first curve axis and a second curve axis orthogonal to the first curve axis, and the optical fiber is arranged on an intersection between the first and second curve axes.

9. The endoscope apparatus according to claim 1, wherein the sensing part for detecting the curved shape of the insertion tube is provided only in a part of the outer periphery of the optical fiber, and the curved-shape detection sensor has a detection direction of a curved shape of the optical fiber that is determined in accordance with an orientation of the sensing part, and the optical fiber is held so that the detection direction is orthogonal to the one or more curve axes.

10. The endoscope apparatus according to claim 9, wherein the one or more curve axes comprises two or more curve axes and the curved-shape detection sensor is provided with a plurality of the sensing parts each detecting the curved shape of the insertion tube, a detection direction of at least one sensing part of the sensing parts is orthogonal to a curve axis of the two or more curve axes having a greater curve angle, and the optical fiber is held so that the at least one sensing part is parallel to the curve axis.

11. The endoscope apparatus according to claim 1, wherein the sensor holding member comprises a channel tube.

* * * * *